United States Patent
Wu

(10) Patent No.: US 6,626,887 B1
(45) Date of Patent: Sep. 30, 2003

(54) HARD TISSUE DRUG DELIVERY DEVICE AND METHOD

(75) Inventor: Gin Wu, Corte Madera, CA (US)

(73) Assignee: IntraVantage, Inc., Plymouth, MN (US)

( * ) Notice: Subject to any disclaimer, the term of this patent is extended or adjusted under 35 U.S.C. 154(b) by 0 days.

(21) Appl. No.: 09/588,425

(22) Filed: Jun. 6, 2000

Related U.S. Application Data

(60) Provisional application No. 60/138,095, filed on Jun. 8, 1999.

(51) Int. Cl.⁷ .................. A61M 31/00; A61G 17/02
(52) U.S. Cl. .................. 604/512; 604/264; 433/80; 433/165
(58) Field of Search .............. 604/28, 243, 264, 604/273, 22, 49, 171, 181, 187, 198, 218, 239, 272, 506, 508, 512, 266, 267; 606/160, 167, 170, 181, 184, 185; 433/80, 82, 165

(56) References Cited

U.S. PATENT DOCUMENTS

| | | | | |
|---|---|---|---|---|
| 5,261,818 A | * | 11/1993 | Shaw ........................ | 433/165 |
| 5,431,655 A | * | 7/1995 | Melker et al. .............. | 604/264 |
| 5,607,435 A | * | 3/1997 | Sachdeva et al. .......... | 359/819 |
| 5,820,609 A | * | 10/1998 | Saito ......................... | 604/264 |
| 6,135,769 A | * | 10/2000 | Kwan ........................ | 433/165 |
| 6,162,203 A | * | 12/2000 | Haaga ....................... | 128/898 |
| 6,210,376 B1 | * | 4/2001 | Grayson ..................... | 604/264 |
| 6,217,561 B1 | * | 4/2001 | Gibbs ......................... | 433/80 |
| 6,419,490 B1 | * | 7/2002 | Kitchings Weathers, Jr. | 433/165 |

* cited by examiner

Primary Examiner—Manuel Mendez
Assistant Examiner—Mark K. Han
(74) Attorney, Agent, or Firm—Welsh & Katz, Ltd.

(57) ABSTRACT

A medication delivery device is disclosed having a hollow drill bit with a lateral opening that is adjacent to a beveled or sharpened tip of a hypodermic needle. The lateral opening, which can be a slot or a notch or hole, is located a distance proximal of the sharpened tip that is not less than the thickness of the tissue to be penetrated. This structure allows the hollow drill to penetrate bone and/or other hard tissues without being completely clogged by drilling debris. After drilling into the bone or hard tissue, medication can be delivered through the bore of the hollow drill. The lateral opening provides a clog-free passage for injection of the medication.

3 Claims, 6 Drawing Sheets

HARD TISSUE DRUG DELIVERY DEVICE AND METHOD

CLAIM OF PRIORITY

This application claims priority from co-pending provisional application 60/138095, filed Jun. 8, 1999.

FIELD OF THE INVENTION

This invention relates to medical apparatus and methods used to deliver medication through or into bone and other hard tissue. In particular, this invention relates to a medication delivery apparatus with a hollow drill bit and a beveled tip with an extended open slot or an open notch or hole at the perforating end. The invention also relates to a method of delivering medication through the hollow drill bit into or through bone and/or other hard tissue after drilling without removing the drill bit.

BACKGROUND OF THE INVENTION

Dentists often conduct local anesthesia to patients to reduce pain during dental procedures. Many dentists and most patients, however, are dissatisfied with the results of traditional anesthetic injection techniques. Problems with administration of anesthetic in traditional injection technique include: slow onset of anesthesia after injection, the long duration and extent of postoperative numbness for patients, especially on children, and the occasional inability to achieve total anesthesia.

One prior art solution was the intraosseous injection technique developed in the early 1900's. The intraosseous injection technique involves 3 simple steps. First, a dentist anesthetizes the gingival tissue topically over the target site of perforation (a point between the problem tooth and the adjacent tooth). Second, the dentist drills through the cortical plate of the jawbone to create a hole. Lastly, local anesthetic solution is injected into the cancellous bone through the hole by regular syringe and needle. The intraosseous injection technique eliminated many of the problems of the traditional injection. The anesthetic took effect quickly and effectively and caused little postoperative numbness. In addition, unlike other techniques, it worked well in almost all patients. However, the intraosseous injection technique had many problems in its early days, including the lack of tools designed for the technique. The technique also produced large holes causing significant bone and soft tissue trauma with increased risk of bone infection.

One prior art improvement of the intraosseous injection technique was developed in late 1980's. It was the Stabident System, which involved the use of a small wire drill (diameter of 0.016 inch, equivalent to 27 gauge). The use of a small drill bit reduced tissue damage and the risk of infection.

In spite of these advantages, the Stabident System has several drawbacks. In particular, dentists were required to switch to a hypodermic needle to inject anesthetic once a hole was drilled with the small drill bit. To identify the location of the hole and aim a very small hypodermic needle through the hole is very difficult because the opening produced by the small drill bit is covered by gingival tissue. Another problem with the Stabident System is that the stainless steel drill bits were not properly tempered. As a result, the drill bits would occasionally wear out prematurely. Worn out drill bits generate excessive heat during use, which may cause heat damage to the surrounding bone tissue. In addition, excessive heat levels occasionally cause meltdown and detachment of the plastic hub attached to the drill bit. This can result in the detached drillhead being left inside the patient's jawbone leading to further complications.

Rotary dental tools with hollow bits have been used in the past as a grinding tool. Such a tool has a low speed and a relatively large-diameter hollow bit for grinding bone while supplying water to the grinding area to lubricate and flush particles. However, this art does not disclose a means to supply anesthetic or medication to a tooth.

An improvement over these techniques was the subject of the U.S. Pat. No. 5,779,708, issued Jul. 14, 1998 and invented by the same inventor as the present invention. The '708 patent relates to a small diameter hollow drill bit that has a removable stylet in place during drilling so that the bore of the drill bit does not become clogged with drilling debris. After the hole is drilled, the stylet is removed and the medication is injected through the hollow drill bit.

SUMMARY OF THE INVENTION

In order to meet these concerns, the present invention is directed to an intraosseous and/or hard tissue drug delivery system that provides an easily identified and accessible drug delivery passage for the operator, thereby, greatly reducing the technical difficulty and extending the potential applications of the intraosseous and/or hard tissue injection technique. In other words, this invention is a hard tissue and/or intraosseous drug delivery system that perforates the hard tissue and also provides a visible and uncovered drug delivery passage through the soft tissue.

The present invention is a medication delivery device that encompasses a hollow drill bit with an open slot that extends from a distal beveled tip toward the proximal end of the drill. This extended slot design allows the hollow drill to penetrate bone and/or other hard tissues without being clogged by the bone or hard tissue debris, as long as the overall length of the bevel and open slot is greater than the thickness of bone and/or hard tissue. After drilling into the bone or hard tissue, medication can be delivered through the hollow drill. The extended length of the open slot provides a clog-free passage for injection of the medication.

An alternative design of this invention is a hollow drill bit with an open notch (a small hole through the wall of the hollow drill) located proximal of the distal beveled tip. As long as the overall distance from the distal tip of the bevel to the open notch is greater than the thickness of cortical bone and/or hard tissue, the hollow drill will not be clogged by the debris from bone and/or hard tissue and medication can be injected into the site.

A feature of this invention is that the extended slot or open notch provides a longer open area of the lumen of the hollow drill than a hollow drill with a beveled tip. In the drilling process with traditional single or double beveled hollow drill, if the length of the bevel is close to or shorter than the thickness of the bone and/or hard tissue, the hollow drill (without a stylet) will be clogged by the debris after the beveled area has submerged into the bone before the drill tip has penetrated to the other side of the dense bone layer. A beveled drill bit with an extended slot, according to the present invention, can drill through the same bone and/or hard tissue without being clogged because the debris from the bone and/or hard tissue will only fill the lumen up to the same length as the thickness of the cortical bone and/or hard tissue. Therefore, the part of extended slot beyond the thickness of the cortical bone and/or hard tissue will stay open for the medication to flow through. With the alternative open notch design, the hollow drill can drill through the bone and/or hard tissue of a thickness less than the length from the drill tip to the distal edge (toward tip end) of the notch without being clogged. After the perforation and while keeping the hollow drill in place, the dentist or practitioner can deliver medication through the hollow drill by using a syringe type device with a hypodermic needle with an O.D. (outer diameter) smaller than the I.D. (inner diameter) of the hollow drill.

An advantage of the present invention is that it provides maximum simplicity and effectiveness to intraosseous drug delivery technology. This invention eliminates the need of a stylet for a hollow drill to prevent the hollow drill being clogged by the bone and/or hard tissue debris during the drilling process. It provides the solution to the current problems of intraosseous injection encountered by dentists in dental anesthesia heretofore. This invention also provides broader applicability of the intraosseous injection technique to dental anesthesia, dental medications and other potential medical applications.

In a preferred embodiment, the hollow drill bit of this medication device is a hypodermic tube having a sharpened point and an extended slot. An alternative structure arrangement is a hypodermic tube having a sharpened point and an open notch or hole through the wall of the hollow drill above (proximal to) the sharpened tip. The blunt end of the hollow drill is embedded in a hub shaped to fit into the chuck of a rotating tool.

The hollow drill bit is preferably sized at 24 G (gauge) so it will produce only a very small hole in the bone. It causes no significant damage to the bone structure. The drill bit is highly hardened and its sharp cutting angle provides a smooth drilling action to prevent the generation of excessive heat. Because the beveled tip makes the hollow drill rotate eccentrically, the diameter of the hole generated by the hollow drill bit is slightly larger than the diameter of the drill bit. This effect, however, allows easy removal of the drill after the injection.

The extended slot in the drill bit allows more uptake of drilling debris without being completely clogged. The alternative open notch design serves the same function as the extended slot hollow drill. The proximal end (opposite end from the distal sharpened tip) of the hollow drill extends outward past the hub and provides an easily identified injection passage for the injection needle.

Before this invention, intraosseous injection techniques in dental anesthesia encountered major difficulties for both patients and dentists. During the early development history of intraosseous injection, reamers or roseheads were used as drill bits. They would cause tremendous bone damage to the patient with greater exposure for potential inflammation and infection. At a later time, a special drill was developed, but the procedure required dentists to find a very small hole under the gum tissue. A potential of mismatching the hole and needle has frustrated many users. Further, because of the limited space and angle accessible to the dentist or operator on the back teeth makes the use much more difficult, therefore, the device is generally limited to the front teeth. The invention described in this document, however, has eliminated all of the above problems. The applicable area expands to the whole mouth, and the small hollow drill will not produce significant bone damage.

This invention is not limited to injecting local anesthetics in dental applications. The invention is broadly usable for injecting a wide range of medications, including antibiotics, and in other medical and veterinary applications.

The features and advantages described in the specification are not all-inclusive. Many additional features and advantages will be apparent to one of ordinary skill in the art in view of the drawings, specifications and claims hereof. Moreover, it should be noted that the language used in the specification has been principally selected for readability and instructional purposes and may not have been selected to delineate or circumscribe the inventive subject matter, or resort to the claims being necessary to determine such inventive subject matter.

DETAILED DESCRIPTION OF THE PREFERRED EMBODIMENTS

The Figures of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
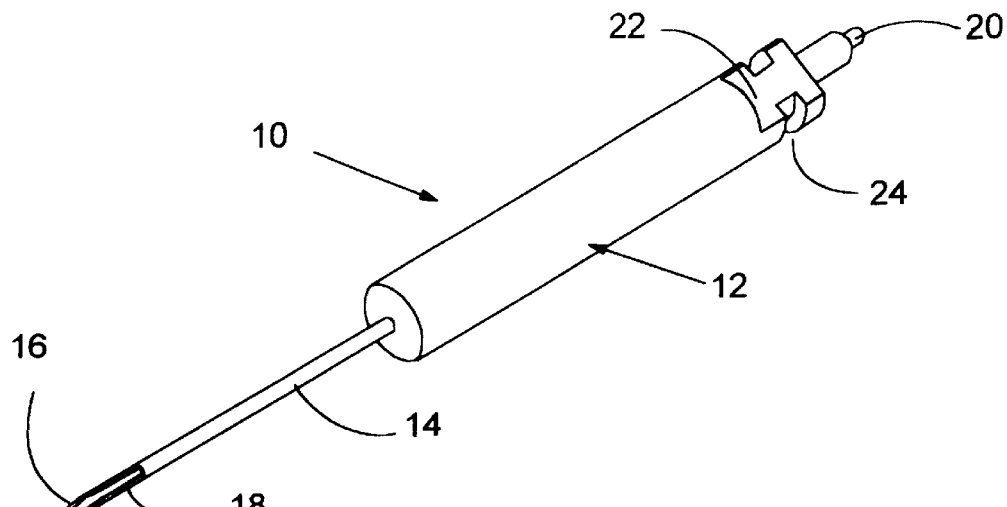
FIG. 1 is a perspective view of a medication delivery device with a hollow drill bit according to one embodiment of the present invention, shown in an assembled state with an extended slot at a beveled tip.
Figure 2:
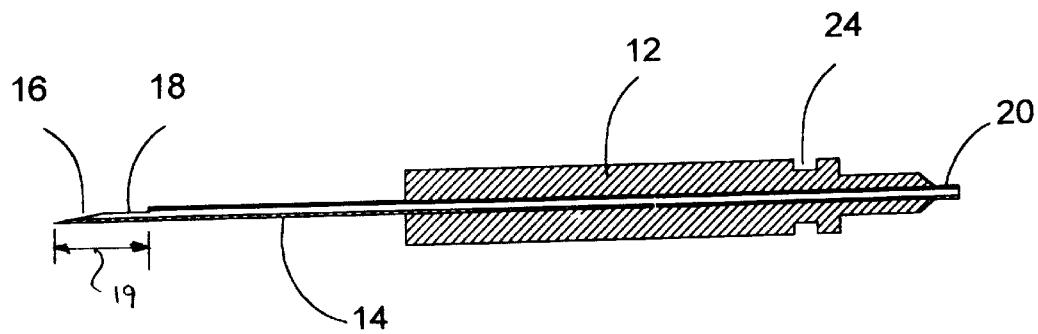
FIG. 2 is a longitudinal section of the hollow drill bit of FIG. 1.
Figure 4:
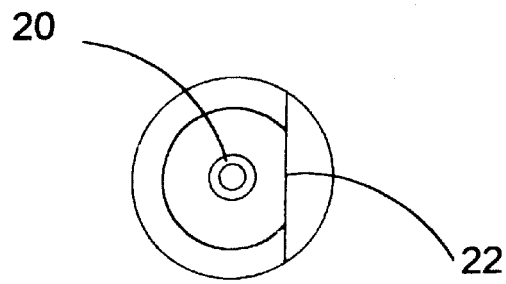
FIG. 4 is an end view from the hub end of the hollow drill bit of FIG. 1.

One aspect of the present invention is a medication delivering device having a hollow drill bit with a slot extending from the sharpened tip. The preferred embodiment of such a medication delivering device 10, shown in FIG. 1, includes a cylindrical hub 12 and a drill bit 14 with a beveled distal tip 16 and, an extended slot 18. The slot extends from the sharpened tip 16 toward the hub. The hollow drill bit extends axially through the entire length of the hub and the blunt proximal end 20 slightly protrudes from the back of the hub as shown in FIG. 1, FIG. 2 and FIG. 4. The dimension of the cylindrical hub and the longitudinal flat area 22 and groove 24 are chosen to match the chuck of the latch head of standard dental handpiece attachment or alternative drilling device. The hub is preferably made of stainless steel, aluminum or plastic.

The hollow drill bit 14 is preferably a 24 G (gauge) hypodermic tubing with a sharpened and hardened distal tip 16. Different sizes of hypodermic tubing are also can be used as long as their I.D. (inner diameter) can be matched by a smaller size standard hypodermic needle. By inserting the smaller hypodermic needle tip of a syringe into the back or proximal end 20 of the hollow drill after the drilling, medication can be delivered into the bone and/or hard tissue through the hollow drill 14.

Figure 3A:
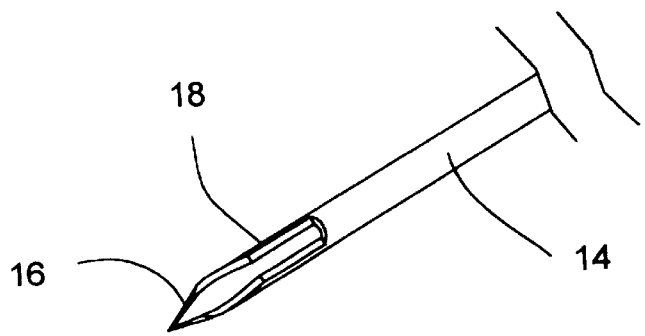
FIG. 3a is an enlarged perspective view of the beveled tip and its extended slot of the hollow drill bit.
Figure 3B:
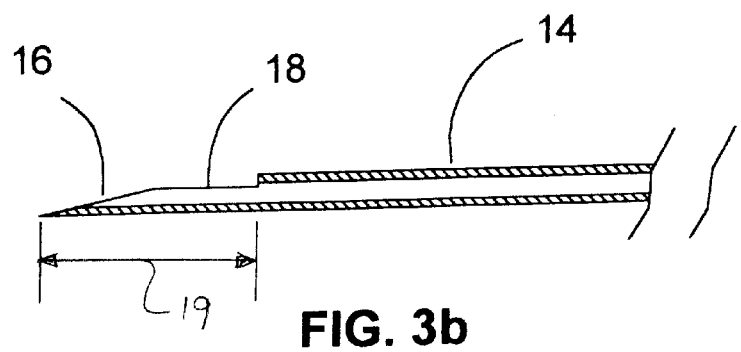
FIG. 3b is a longitudinal section of the tip of the hollow drill bit of FIG. 1.

As shown in FIG. 3a and FIG. 3b, the slot 18 is extended axially from the bevel 16 toward the hub 12. The slot should be sized with consideration given to the strength of the tip of the drill bit. The length of the slot 18 will be determined by the thickness of the target bone and/or hard tissue. The length of the open slot plus the length of the bevel should always be larger than the thickness of the targeted cortical bone and/or hard tissue. For intraosseous applications using a 24 G drill bit, for example, the slot 18 is about 0.10 to 0.125 inch measured from the distal tip to the proximal end of the slot, as shown as distance 19 in FIGS. 2 and 3b.

An alternative embodiment of the medication delivery device is shown in FIG. 8–12b. Instead of making an extended slot on the tip of the medication delivery device 30, a small open notch or hole 38 is made proximally of the beveled tip 36 toward the hub end 32 by cutting through the wall of the hollow drill bit 34. The hollow drill body extends through the entire hub with the blunt end 40 slightly protruding from the back end of the hub. The flat portion 42 and the groove 44 at the end of the cylindrical hub serve as mating structure to the chuck of standard dental handpiece attachment. The length from the sharpened tip to the open notch 38 should always be larger than the thickness of the targeted cortical bone and/or hard tissue. For intraosseous applications using a 24 G drill bit, for example, the notch or hole 38 is about 0.10 to 0.20 inch measured from the distal tip to the center of the notch or hole, as shown as distance 39 in FIGS. 9 and 10b. In that application, the notch or hole 38 has an opening of about 0.005 to 0.008 inch across.

A method and the working mechanism of using the medication delivery device 10 according to the present invention will know be described with reference to FIG. 5a–5b, FIG. 6, FIG. 7 and FIG. 12a–12b. The hollow drill is packaged and sterilized and is installed into the spindle chuck of a regular latch-head dental handpiece attachment 52 (Fig.6). The blunt proximal end 20 extends out the backside of the spindle chuck of the dental handpiece attachment.

Figure 6:
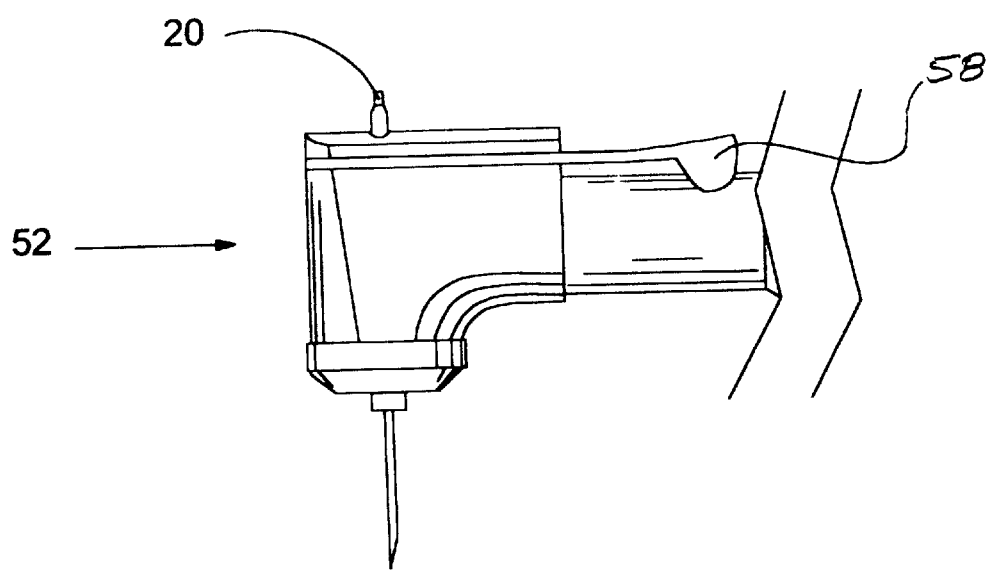
FIG. 6 is a prospective view of the hollow drill bit of the present invention installed into the spindle chuck of a latch-head dental handpiece attachment with the blunt end extending through the back of the spindle chuck of the dental handpiece attachment.
Figure 7:
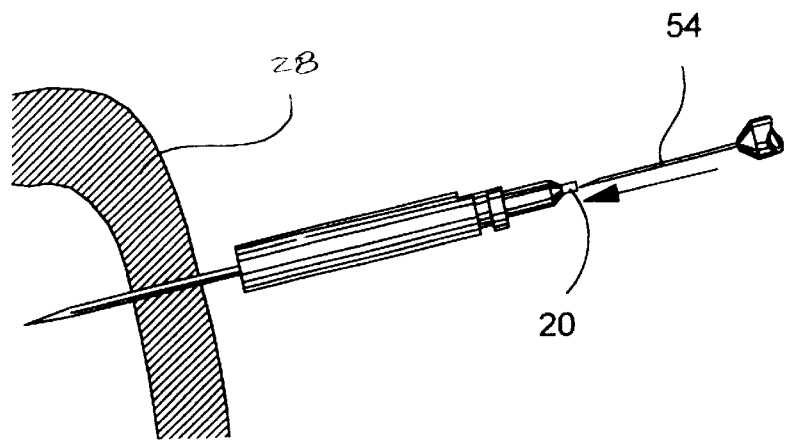
FIG. 7 is a view partially in section of the hollow drill bit of the present invention penetrating through cortical bone. A small size hypodermic needle is fitted into the bore of the hollow drill to deliver the medication through the bore of the hollow drill.
Figure 8:
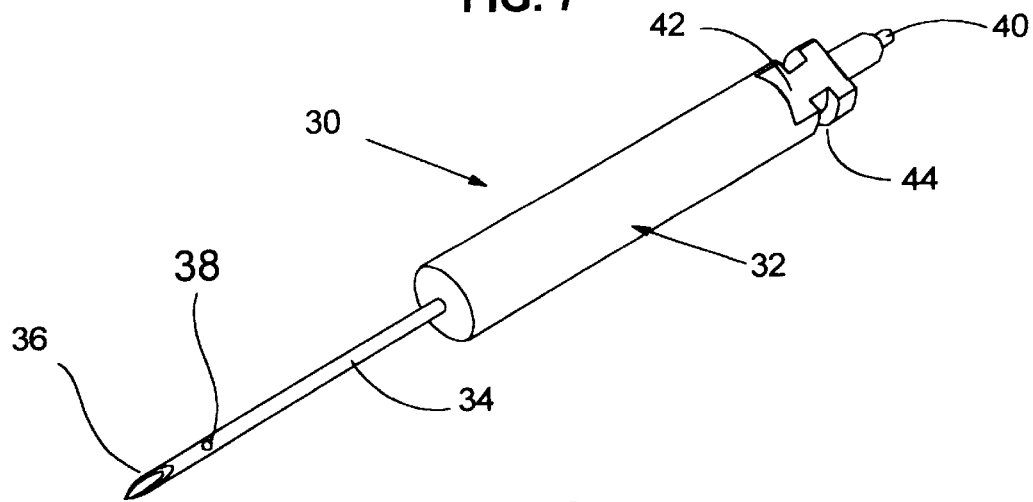
FIG. 8 is a perspective view of another embodiment of the medication injection device of the present invention, which has an open notch on the wall of the hollow drill bit above the sharpened tip.
Figure 9:
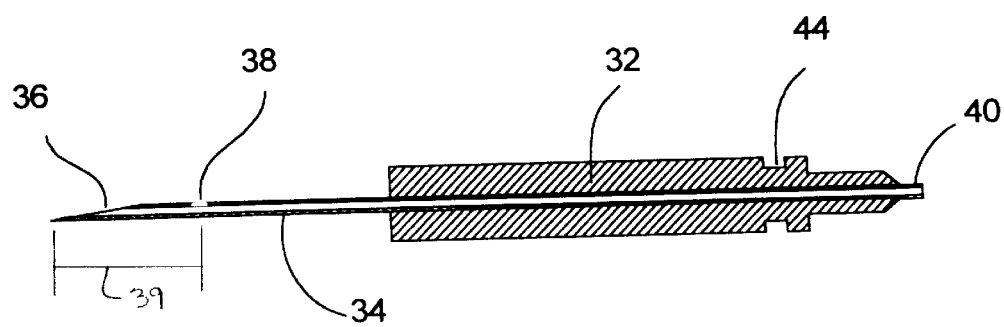
FIG. 9 is a longitudinal section of the hollow drill bit of FIG. 8.
Figure 10A:
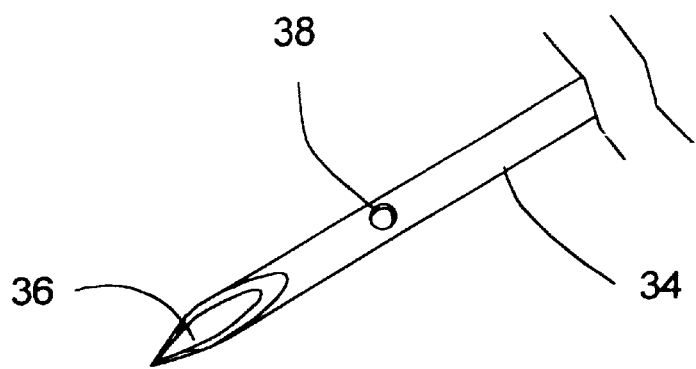
FIG. 10a is an enlarged perspective view of the beveled tip and the open notch of the hollow drill bit of FIG. 8.
Figure 10B:
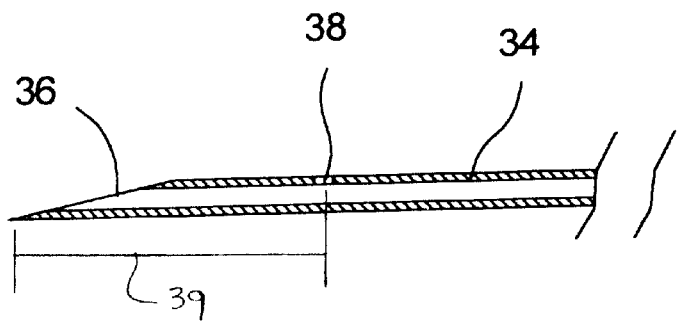
FIG. 10b is a longitudinal section of the tip of the hollow drill bit of FIG. 8.
Figure 11:
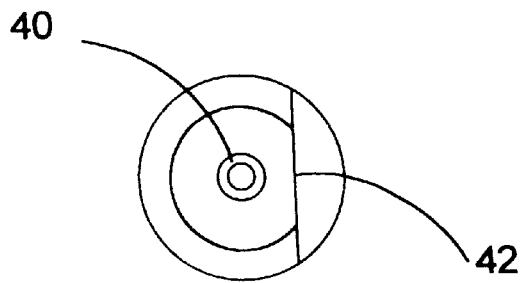
FIG. 11 is an end view from the hub end of the hollow drill bit.

After the medication delivery device 10 is installed in the handpiece, the device is ready for use. Once the desired perforation site is selected, the handpiece is activated and the hollow drill 14 drills into the subject. When the drilling is complete, the hub 12 of the medication device is released from the handpiece by open the latch 58 (FIG. 6). The operator inserts the tip 54 of a hypodermic syringe containing medication into the bore of the blunt end 20 of the hollow drill bit 10 and delivers medication through the bore of the hollow drill (FIG. 7). After the injection is complete, operator removes the drill either by hand or by other holding tools.

An alternative procedure can be chosen by the operator. The operator directly inserts the tip of the hypodermic syringe into the bore of the blunt end 20 of the hollow drill bit 10 while operator holds the handpiece 52 steadily. After the injection is complete, operator withdraws the device by directly removing the handpiece.

Figure 5A:
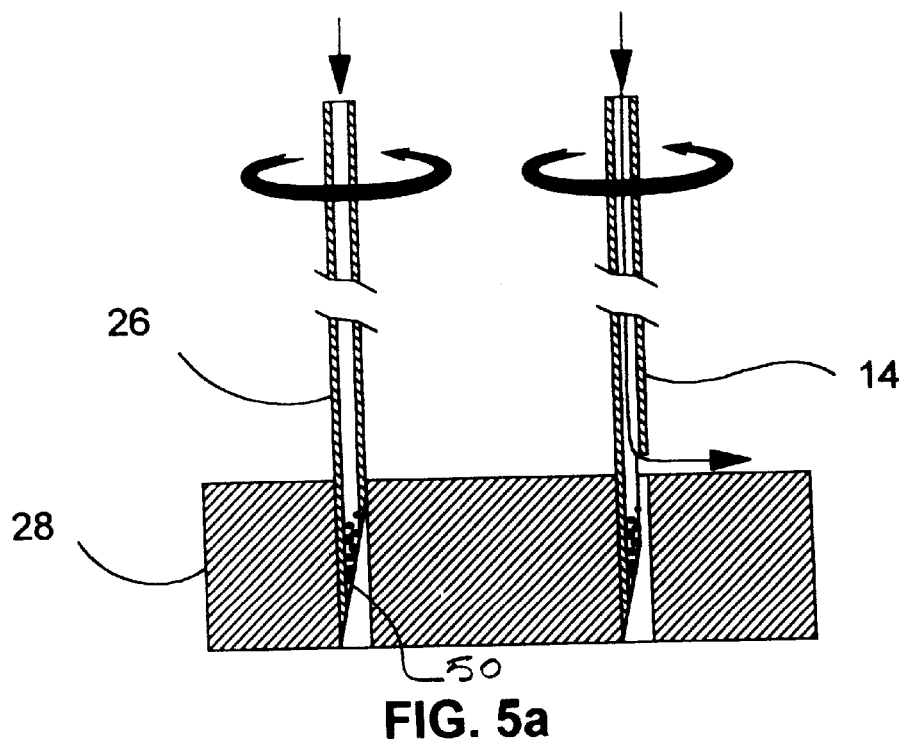
FIG. 5a illustrates the distribution of debris at the hollow drill tip during drilling process. The passage of the hollow drill of the present invention (right) stays open during the drilling process. The conventional beveled hollow drill (left) is clogged by the debris when its beveled area is within the bone wall during the drilling.
Figure 5B:
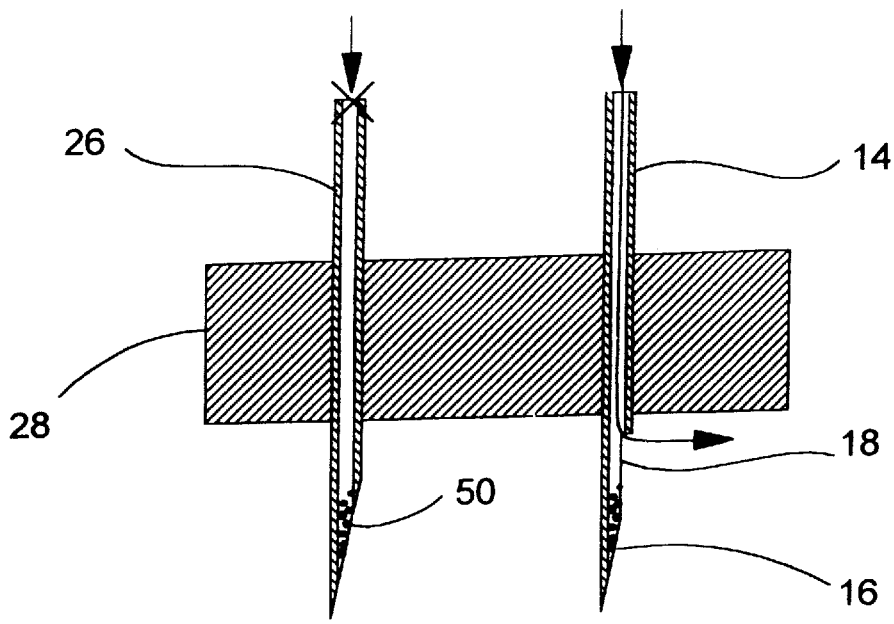
FIG. 5b illustrates the distribution of debris at the hollow drill tip after drilling process. The passage of the hollow drill of the present invention (right) stays open after drilling. The conventional beveled hollow drill (left) stays clogged by the debris after drilling.

A detailed description of the mechanism of the medication delivery device that stays unclogged by the debris after drilling through the targeted bone and/or hard tissue is shown in FIGS. 5a–5b. During the drilling process, if the thickness of the cortical bone and/or hard tissue 28 is greater than the bevel length of the conventional single or double beveled hollow drill 26, the hollow drill 26 would be completely clogged by the debris 50 (FIG. 5a) when the whole beveled area is submerged in the cortical bone. Therefore, after the drilling process, the hollow drill can no longer be used as medication delivery passage without unclogging the tip by using other methods. The hollow drill 14 with extended slot of the present invention, however, can stay open during (FIG. 5a) and after (FIG. 5b) drilling through the target tissue. The operator can continue the procedure by delivering medication through the bore of the hollow drill (FIG. 7).

Figure 12A:
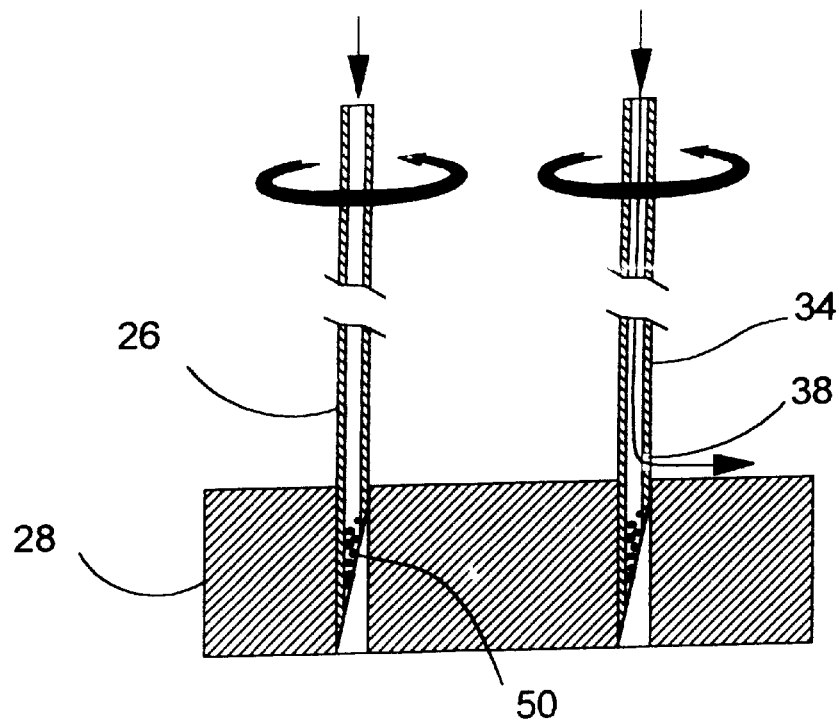
FIG. 12a illustrates the distribution of debris at the hollow drill tip during drilling process. The passage of the hollow drill bit described in this invention (right) stays open during the drilling. The conventional beveled hollow drill (left) is clogged by the debris after its beveled area is within the cortical bone during the drilling.
Figure 12B:
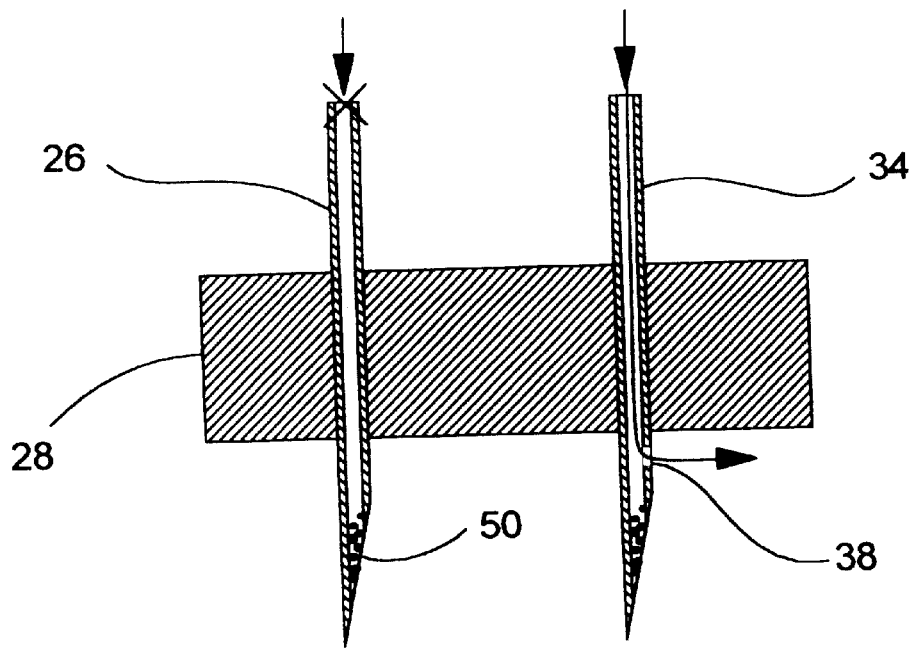
FIG. 12b illustrates the distribution of debris at the hollow drill tip after drilling process. The passage of the hollow drill described in this invention (right) stays open after drilling. The conventional beveled hollow drill (left) stays plugged by the debris after drilling.

The same mechanism of the alternative embodiment of the medication delivery device described by FIG. 8–11 is shown in FIGS. 12a–12b. During the drilling process, a conventional hollow drill 26 will be clogged by the debris 50 (FIG. 12a) after the whole beveled area submerging below the surface of the bone, if the thickness of the subject is greater than the length of the bevel. Under the same condition, the present invention of a hollow drill 34 with an open notch 38 proximal of the beveled tip stays open during. (FIG. 12a) and after (FIG. 12b) drilling through the target tissue and continue serve as a medication delivery passage (FIG. 7).

Since the hollow drill design provides an easily identified drug delivery passage passing through the covering soft tissue, this device has many advantages over other devices. In comparison to the rosehead burr or reamer, the present invention will drill a smaller hole, similar to the diameter of an ordinary 24 G needle. Therefore, bone and tissue damage is significantly reduced. In comparison to the perforator and hypodermic needle used in Stabident System, the present invention provides a clearly visible passage on the surface of the soft tissue for delivering medication. Therefore, there is no need to use trial and error to find the tiny hole on the bone under the soft tissue. Also if it is necessary, operator may temporarily leave the hollow drill in the position by removing the dental handpiece after releasing the latch. This will provide the operator with the opportunity to dispense more dosages to the same location. In comparison to a hollow drill with a stylet for intraosseous injection, this device provides a simpler and faster procedure and also greatly reduces the instability of handling the device caused by removing the stylet.

The application field of this invention includes, but is not necessarily limited to, dental, medical and veterinary medicine.

While the invention has been disclosed with reference to drilling holes between teeth to apply medication for dental anesthesia, those skilled in the art will recognize that the invention will be useful for any procedure requiring the drilling of an opening-and the delivery of fluid into tissue. From the above description, it will be apparent that the invention disclosed herein provides a novel and advantageous medication injection device and associated method. The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A method of administering medication to a target tissue through a predetermined thickness of bone or hard tissue and subsequently injecting medication through the bone or hard tissue to the target tissue, said method comprising the steps of:

drilling an opening in the tissue with a drilling device, wherein the drilling device includes a hollow drill bit having a sharpened tip and an axial opening at one end thereof and a bore extending therethrough, wherein the hollow drill bit further includes a lateral opening to the bore that is located at a distance from the sharpened tip that is not less than the thickness of the bone or hard tissue to be drilled by the device, wherein the sharpened tip has a beveled surface, wherein the lateral opening is an axially-extending slot extending a distance in the range of from about 0.10 to about 0.125 inch measured from the distal tip of the hollow drill bit to the proximal end of the slot that is open to the bore of the hollow drill bit, and wherein the distance from the distal end of the sharpened tip to a proximal end of the slot is greater than the length of the beveled surface along the axis of the bore such that the lateral opening does not become blocked with bone or hard tissue during drilling;

keeping the lateral opening slot free of tissue debris, and before withdrawing the needle from the bone or hard tissue through which it has been drilled, injecting medication through the bore of the hollow needle wherein medication flows out of the lateral opening of the hollow drill bit and into the target tissue.

2. A method as recited in claim 1 wherein said bone or hard tissue is bone, cartilage or tendon, wherein the axial opening and the lateral opening merge into an opening to the bore extending along the axis of the hollow drill bit, and wherein said medication is injected by inserting a needle to a syringe into the bore at an end opposite the sharpened tip, wherein the syringe has medication to be administered to the tissue, and injecting medication from the syringe and through the bore of the hollow drill bit, wherein the medication flows out of the lateral opening of the hollow drill bit and into the tissue.

3. A method as recited in claim 1 wherein the medication is a local anesthetic.

\* \* \* \* \*